United States Patent [19]

Krol et al.

[11] 4,184,252
[45] Jan. 22, 1980

[54] OVERDENTURE AND METHOD FOR SECURING SAME

[75] Inventors: Arthur J. Krol, 600 21st Ave., San Francisco, Calif. 94121; Tomas C. Pablos, San Francisco, Calif.

[73] Assignee: Arthur J. Krol, San Francisco, Calif.

[21] Appl. No.: 853,004

[22] Filed: Nov. 18, 1977

[51] Int. Cl.² ........................................... A61C 13/00
[52] U.S. Cl. .................................................. 433/172
[58] Field of Search ............... 32/2, 10 A, 13, DIG. 6

[56] References Cited

U.S. PATENT DOCUMENTS

| | | | |
|---|---|---|---|
| 2,149,048 | 2/1939 | Freedman | 32/2 |
| 3,085,334 | 4/1963 | Bischof et al. | 32/10 A |
| 3,646,676 | 3/1972 | Mitchell | 32/2 |

FOREIGN PATENT DOCUMENTS 2308348  12/1976  France ............................ 32/DIG. 6

*Primary Examiner*—Robert Peshock
*Attorney, Agent, or Firm*—Townsend and Townsend

[57] ABSTRACT

An improved overdenture structure and a method for securing it to the residual ridge of a patient. The nerve of at least one healthy tooth is removed and the root canal is filled with dental paste as in a root canal treatment. The crown of the tooth is removed near the gum line and a ferromagnetic bar is embedded in the filled root. Magnetic material is embedded in the overdenture in such position as to be aligned with the ferromagnetic bar at closure points. The dental material surrounding the ferromagnetic bar and the magnetic material embedded in the overdenture are shaped so as to provide contoured mating surfaces with one another. In an alternative embodiment, a root canal treatment is performed on two healthy teeth and bars are embedded in the roots of those teeth. A ferromagnetic rod is connected between the ends of the two bars. Magnetic material is embedded in the overdenture in position to be aligned with the entire length of the ferromagnetic rod. The dental material surrounding the ferromagnetic bars and the magnetic material embedded in the overdenture are shaped so as to provide contoured mating surfaces with one another.

8 Claims, 4 Drawing Figures

OVERDENTURE AND METHOD FOR SECURING SAME

BACKGROUND OF THE INVENTION

1. Field of the Invention

The present invention relates to a method for securing an overdenture in an oral position and to an improved overdenture structure. More specifically, the invention relates to the securing of an overdenture by magnetic attraction between the overdenture and the remaining natural teeth. The nerves of the remaining natural teeth are removed and the roots filled with dental paste as in a root canal treatment. The crowns of the teeth are removed and ferromagnetic material is embedded in the roots.

Overdentures are artificial dentures which attach over one or more natural teeth which have had the crowns removed and the roots filled as in a root canal treatment. It has long been known in dentistry that overdentures are preferred over ordinary artificial dentures. Thus, if the dentist determines that one or more of the patient's natural teeth can be saved, a root canal treatment is performed and the crowns of those teeth are removed. The remaining portions of the natural teeth are then ground to provide a contoured mating surface with the overdenture. The overdenture is then formed to fit over the residual ridge of the patient and over the remaining natural teeth which have been subjected to the above treatment. An advantage of an overdenture is that it permits the patient to apply a much greater biting pressure before pain is induced. Furthermore, the retention of one or more natural teeth prevents resorption of the jaw bone.

2. Description of the Prior Art.

In normal dental practice, an overdenture is secured by reliance on conventional adhesive and cohesive forces created by the close fitting of the overdenture to the residual ridge. When such normal retention is not available because of factors peculiar to the patient, adhesives are used.

Commercially available adhesives lose their adherence over a period of time. The adhesive most frequently fails when a patient is either talking or eating, thus subjecting the patient to embarrassment. Furthermore, adhesives create unsanitary conditions in the patient's mouth which can be irritating and damaging.

Mechanical attachments, such as the Zest anchor, are available to secure overdentures. These mechanical means are fragile and make the removal of the overdenture cumbersome.

The present invention is directed to an improved overdenture and to a method employing magnetic attraction for securing an overdenture to the residual ridge which eliminates the problems presented by the use of adhesives and mechanical attachments.

U.S. Pat. Nos. 2,543,773 and 2,555,392 disclose the use of magnets embedded close to the biting surface of ordinary artificial dentures. The magnets are embedded in respective upper and lower artificial dentures and aligned so that identical poles of the magnets are opposite one another. The resulting repelling forces of the magnets push the dentures against the residual ridges of the patient, thus serving to aid in securing the artificial dentures in the oral position.

U.S. Pat. Nos. 3,514,859 discloses a magnet surgically implanted into the body of the jaw bone and opposing a second magnet of opposite polarity which is attached to an ordinary artifical denture.

SUMMARY OF THE INVENTION

The present invention comprises an improved overdenture and a method for securing it to the residual ridge of a patient. Quite frequently it is found that the patient to be fitted with artificial dentures has one or more teeth that can be saved. In such an instance, the nerves of those teeth are removed from the roots, and the roots filled with dental paste or other suitable material as in a root canal treatment. The crowns are then removed near the gum line. The teeth are then ground to provide a contoured surface. An artificial denture, called an overdenture, is molded to fit over the residual ridge and the remaining natural teeth which have been subjected to the above treatment. Overdentures can be either partial or full, depending on how many of the patient's teeth must be removed.

The present invention is directed to an improved overdenture and a method for securing the overdenture to the residual ridge of a patient by magnetic means. The method of securing the overdenture involves using a ferromagnetic bar or pin in the roots of remaining natural teeth in a position so as to be aligned with magnetic material in the overdenture. The remaining natural teeth and the portions of the overdenture in which the magnetic material is embedded are shaped so as to provide contoured mating surfaces with one another.

In an alternative embodiment, a root canal treatment is performed on at least two natural teeth and the crowns of those teeth removed near the gum line. Bars or pins, which need not be ferromagnetic, are then inserted into the roots and a ferromagnetic rod is connected to the ends of the two bars so as to provide a larger magnetic attracting surface. The rod is attached to the ends of the two bars by soldering or cementing. Magnetic material of the same length as the ferromagnetic rod and of a contour to mate with the ferromagnetic rod is then embedded in the overdenture to be aligned with the ferromagnetic rod. Alternatively, a unitary ferromagnetic rod with ends bent at approximately right angles can serve as the rod soldered to the two bars. In this embodiment, a much greater magnetic attraction is produced because of the greater surface area contacted.

Various types of magnetic material are available which produce sufficient magnetic force. Examples of such material are praseodymium cobalt and samarium cobalt. The preferred ferromagnetic material is a steel alloy. The exposed ends of the steel alloy and the magnetic material can be plated with chrome, gold or other suitable material to prevent corrosion. Alternatively, the bars and rod attached to the remaining natural teeth can be made of magnetic material and the material embedded in the overdenture can be made of ferromagnetic material.

The use of the above magnetic means to secure an overdenture to the residual ridge and the remaining natural teeth of a patient provides great advantages over the prior adhesive method. The magnetic forces do not weaken over a period of time and thus the patient can confidently wear the overdenture for a longer period.

It has been found that the most successful embodiment of the improved overdenture and the method for securing it occurs when the two canine teeth and two molars located on opposite sides are retained in a patient's mouth. Such an embodiment provides four separate points at which magnetic forces can be used to hold the overdenture in place.

The novel features which are believed to be characteristic of the invention, together with further objects and advantages thereof, will be better understood from the following description considered in connection with the accompanying drawings in which preferred embodiments of the invention are illustrated by way of example. It is to be expressly understood, however, that the drawings are for the purpose of illustration and description only and are not intended as a definition of the limits of the invention.

DESCRIPTION OF THE PREFERRED EMBODIMENT

Figure 1:
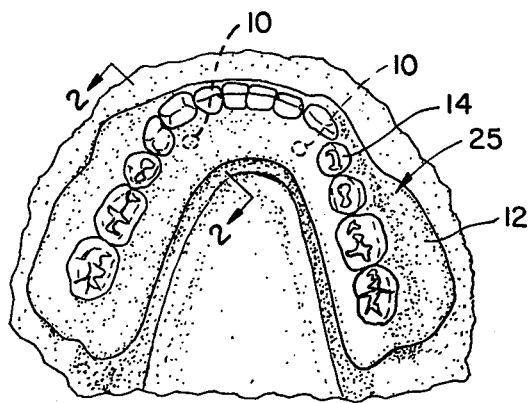
FIG. 1 is a view from above of an improved lower overdenture.
Figure 2:
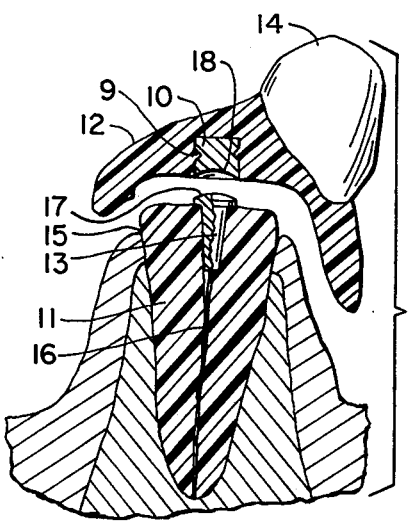
FIG. 2 is a cross-section in line 2—2 of FIG. 1 illustrating the ferromagnetic bar embedded in the natural tooth and the magnetic material embedded in the overdenture.

The improved overdenture is illustrated in FIG. 1 as a lower overdenture. The overdenture is a typical overdenture 25 except that the improvement comprises magnetic material 10 embedded in the underside thereof. The magnetic material 10, in FIG. 2, is embedded in the artifical structure 12 which supports the artificial teeth 14. The magnetic material 10 contains a groove 9 about its circumference to aid its retention within the material comprising the structure 12. The material of structure 12 is of a plastic nature which enables the insertion or embedding of the magnetic material during the manufacturing process. The magnetic material may also be secured within the structure 12 by means of a dental cement.

The cross-sectional view in FIG. 2 illustrates the ferromagnetic bar 13 embedded in the remainder of the natural tooth 11. The natural tooth 11 results from a root canal treatment. The nerve of the tooth which would lie within the canal 16 has been removed. The crown of the tooth has been removed slightly above the gum line 15. A dental paste or other suitable dental fill material is applied inside the canal together with the ferromagnetic bar 13. Also shown in FIG. 2 are the rounded or convex surface 17 of the ferromagnetic bar and the concave surface 18 of the exposed ends of the magnetic material. Alternatively, the bar 13 can be of magnetic material and the magnet 10 can be replaced by ferromagnetic material. The ferromagnetic bar 13 is secured within the natural tooth by cement. Using a ferromagnetic bar containing ridges around the circumferences provides additional frictional securing forces. While the ferromagnetic material is shown embedded in the tooth in the preferred embodiment, other methods of securing are possible. For example, the material could be shaped as a cap and cemented over the entire exposed surface of the tooth.

Figure 3:
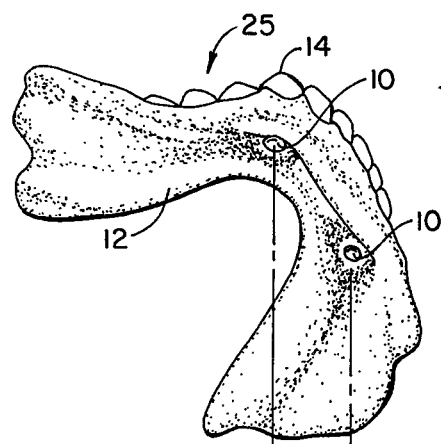
FIG. 3 is an exploded view illustrating the alignment of the improved overdenture with the natural teeth containing the ferromagnetic material.

FIG. 3 illustrates one embodiment of the invention. This embodiment employs two natural teeth with ferromagnetic bars inserted therein. In the preferred method of manufacturing the improved overdenture, an impression is made of the residual ridge 20 and the natural teeth 22 and 24. The making of such an impression is well known in dentistry. After the impression has been made, the dentist is then able to determine the position where the magnetic material 10 should be embedded in the overdenture 25 in order to provide proper alignment and mating with the residual ridge and with the ferromagnetic bars inserted in the remaining natural teeth.

Figure 4:
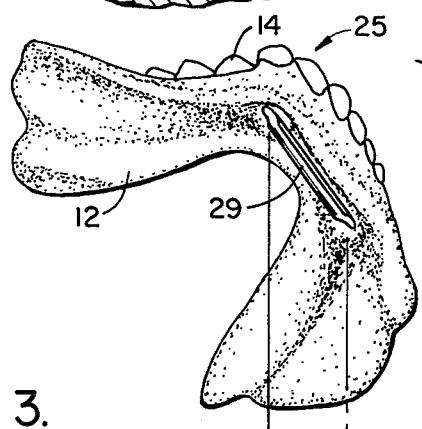
FIG. 4 is an alternative embodiment illustrating a ferromagnetic rod connecting the ends of two ferromagnetic bars and aligned with magnetic material in the overdenture.

An alternative embodiment is illustrated in FIG. 4. This embodiment uses a ferromagnetic rod 27 connecting the ends of two bars or pins 26 and 28. The bars 26 and 28 need not be ferromagnetic. The ferromagnetic rod 27 is typically of circular cross-section and is soldered to the ends of the two pins 26 and 28. This alternative method can be used with more than two teeth by merely connecting the rod to the ends of the bars embedded in each of the teeth. Alternatively, the rod 27 and the pins 26 and 28 can be incorporated into one structure by bending the ends of the rod and inserting the ends into the root canals of the teeth. With the latter structure, soldering would not be required. Magnetic material 29 is embedded in the overdenture 25, also by cementing. The preferred cross-section of the magnetic material 29 is semicircular so as to mate with the cylindrical ferromagnetic rod 27.

While preferred embodiments of the present invention have been illustrated in detail, it is apparent that modifications and adaptations of those embodiments will occur to those skilled in the art. However, it is to be expressly understood that such modifications and adaptations are within the spirit and scope of the present invention as set forth in the following claims.

What is claimed is:

1. An improved overdenture wherein the improvement comprises a first material secured to the overdenture at locations where said overdenture is adapted to be in direct physical contact with a second surface contoured material partially embedded in and extending between at least two natural teeth, wherein said first material and said second material are magnetically attractive to one another, the outer surface of said first material being contoured to mate with that portion of the contoured surface of the second material that extends between said at least two natural teeth.

2. An improved overdenture as recited in claim 1, wherein said first material is magnetic.

3. An improved overdenture as recited in claim 1, wherein said first material is samarium cobalt.

4. An improved overdenture as recited in claim 1, wherein said first material is praseodymium cobalt.

5. A method of securing an overdenture at least two natural teeth each having a root canal with a nerve therein which comprises the steps of:
  (a) removing said nerve from each of said root canals,
  (b) filling said root canals with dental fill material,
  (c) removing the crown of each of said teeth,
  (d) embedding a ferromagnetic bar in each of said root canals,
  (e) attaching a ferromagnetic rod to the ends of said ferromagnetic bars, and
  (f) embedding magnetic material in said overdenture in position so as to be aligned and in direct contact with said ferromagnetic rod.

6. A method as recited in claim 5, further comprising the step of providing the exposed end of said magnetic material with a chrome plating.

7. A method as recited in claim 5, wherein the step of attaching comprises the step of soldering the ends of said ferromagnetic rod to the ends of said ferromagnetic bars.

8. A method as recited in claim 5, further comprising the step of providing the exposed surfaces of said magnetic material with a chrome plating.

* * * * *